(12) United States Patent
Rando et al.

(10) Patent No.: US 7,534,446 B2
(45) Date of Patent: May 19, 2009

(54) SOLID COSMETIC

(75) Inventors: Pietro Rando, Opera (IT); Giuseppe Maio, Zelo Surrigone (IT)

(73) Assignee: Intercos Italia SPA, Milan (IT)

( * ) Notice: Subject to any disclaimer, the term of this patent is extended or adjusted under 35 U.S.C. 154(b) by 0 days.

(21) Appl. No.: 10/199,340

(22) Filed: Jul. 19, 2002

(65) Prior Publication Data

US 2003/0026821 A1 Feb. 6, 2003

(30) Foreign Application Priority Data

Jul. 19, 2001 (IT) .......................... MI2001A1532

(51) Int. Cl.
*A61Q 1/02* (2006.01)
*A61Q 1/04* (2006.01)
*A61Q 1/08* (2006.01)
*A61Q 1/10* (2006.01)

(52) U.S. Cl. ........................................ 424/401; 424/64

(58) Field of Classification Search ................. 424/401, 424/69, 78.02, 63, 64
See application file for complete search history.

(56) References Cited

U.S. PATENT DOCUMENTS

| 3,969,087 | A | * | 7/1976 | Saito et al. | |
|---|---|---|---|---|---|
| 5,462,737 | A | * | 10/1995 | Pfleuger | 424/401 |
| 5,622,693 | A | * | 4/1997 | Funatsu | 424/69 |
| 5,733,534 | A | * | 3/1998 | Sawin et al. | |
| 5,843,407 | A | * | 12/1998 | El-Nokaly et al. | |
| 5,908,631 | A | * | 6/1999 | Arnaud et al. | 424/401 |
| 6,214,329 | B1 | * | 4/2001 | Brieva et al. | |
| 6,423,324 | B1 | * | 7/2002 | Murphy et al. | 424/401 |

FOREIGN PATENT DOCUMENTS

EP   0 795 322 A1  *  9/1997

OTHER PUBLICATIONS

JP- 0335353 abstract (1988).*
Cellulose Ether/FAtty Acid Solutions Show Synergistic Thickening Behavior. Research Disclosure, Kenneth Mason Publications, vol. 233, No. 39. Sep. 1983.*

* cited by examiner

*Primary Examiner*—Jyothsna A Venkat
(74) *Attorney, Agent, or Firm*—Novak Druce & Quigg; J. Rodman Steele; Gregory Lefkowitz

(57) ABSTRACT

The present invention refers to a solid, preferably transparent cosmetic product. In one embodiment the solid cosmetic product comprises: from 0.5% to 30% of at least one alkyl ether from polysaccharides; from 0.1% to 55% of at least one dibutyl lauroyl glutamide or derivatives; and from 1% to 95% of non-polar organic liquids.

2 Claims, No Drawings

SOLID COSMETIC

The present invention refers to a solid, preferably transparent cosmetic product. In particular it refers to a cosmetic product of the type used for lipsticks and sticks for the face, lips, eyes, cheeks and the body.

Solid structures are widely used in the pharmaceutical and cosmetic sectors. The appeal and the purity that transparent structures emanate to the users is certainly an opportunity that cosmetic products should not miss. Solid structures are already known that obtain from the gelation of non-polar organic liquids (natural or synthetic oils) by means of the aggregation or the cross-linking of medium-sized molecules or polymeric structures.

For example the patent U.S. Pat. No. 3,969,087 describes a composition comprising non-polar organic liquids and N-acyl amino acids or derivatives.

In view of the state of the technique described, one object of the present invention is to provide a solid, preferably transparent, cosmetic product, which is pleasant to apply, easy to use, and has a structural and surface stability over a medium-long term.

In accordance with the present invention, these and other objects are reached by means of a solid cosmetic product comprising:

a) from 0.5% to 30% of at least one alkyl ether from polysaccharides or derivatives;

b) from 0.1% to 55% of at least one dibutyl lauroyl glutamide or derivatives;

c) from 1% to 95% of non-polar organic liquids.

Thanks to the gel forming synergy of the present invention a solid, preferably transparent, cosmetic product can be produced which is of pleasant appearance and is easy to use.

The Applicant has surprisingly found that the synergy given by the combination, in the above-described quantities, of the alkyl ethers from polysaccharides, of dibutyl lauroyl glutamide and of the non-polar organic liquids, and in particular by the use of the alkyl ethers from polysaccharides, enables a gelled product to be obtained which has a high quality, particularly in reference to the characteristic of being easy to handle, compact, resistant to temperature variations and mechanically resistant. This is believed to be due to a three-dimensional structure for the formation of hydrogen bridges between the polysaccharidic etherified structure and the carboxylic and amino polar groups of the dibutyl lauroyl glutamide (or its derivatives). This structure generates a mobile cross-link for the intrinsic characteristic of said bridges but stable, where the non-polar organic liquids fill the cells formed in turn developing unstable links that stabilize the entire molecular architecture.

Part a) of the composition can preferably comprise as alkyl ether from polysaccharides, elements or combination of elements selected from the ethyl cellulose family, such as the product ETHOCEL from the company Dow Chemical or the product AQUALON ethyl cellulose from the company Aqualon.

Part b) of the composition can preferably comprise as dibutyl lauroyl glutamide, N-acyl amino acids or derivative elements or combinations of elements selected from the N-acyl amino acids family, such as GP1 from the company Ajinomoto.

For example the N-acyl amino acids family can contain elements or combinations of elements selected among aspartic acid, glutamic acid, glutamine, glycin, alpha-alanine, beta-alanine, alpha-aminobutyric, valine, leucine, isoleucine phenylalanine, serine, threonine, cysteine, methionine, delta-acylornithine, epsioln-acyllysine, gamma-aminovaleric acid, omega-caproic acid.

Preferably part c) of the composition, that is the non-polar organic liquids, in accordance with the present invention has a dielectric constant less than or equal to 20.

The composition can preferably comprise as non-polar organic liquids elements or combinations of elements selected from among the families of aliphatic or aromatic ethers, aliphatic alcohols, aliphatic mono or polyglycerides, alkanes and polyolephins, silicones, oxyalkylatealkyl esters or ethers, totally unsaturated, totally or partially hydrogenated vegetable oils.

For example as aliphatic or aromatic ethers it can contain elements or combinations of elements selected from among ethylesyl palmitate, ethylesyl stearate, ethylesyl isonanoate, isostearylisostearate, octyldodecyl steaoroylstearate, diethylesyl neopentyl glycol, pentaerythritil tetraisostearate, octyldodecyl lactate, diisostearyl malate, trimethyolpropane triethylesyl, capryl coccoate, ethyl macadamiate, diethylesyl adipate, propylene glycol monoisostearate, diethylesylsebacate.

For example as aliphatic alcohols it can contain elements or combinations of elements selected from among octyldodecanol, hexyl dodecanol, oleyl alcohol, cetyl alcohol, isostearyl alcohol.

For example as aliphatic mono or polyglycerides it can contain elements or combinations of elements selected from among glyceryl triethylesyl, hexanoate, glyceryl triisostearate, glyceryl dilaurate, glyceryl monopalmitate, diglyceryl diisostearate.

For example as alkanes and polyolephins it can contain elements or combinations of elements selected from among isodecane, isohexadodecane, polybutene, hydrogenated polyisobutene, polithecene, phytosqualane.

For example as silicones it can contain elements or combinations of elements selected from among dimethicones, cyclopentasiloxane, polydiphenyldimethicone, polycetyldimethicone, acryldimethicone copolymer.

For example as oxyalkylatealkyl esters o ethers it can contain elements or combinations of elements selected from among peg 8 laurate, ppg 7 buthyl ether, ppg 30 cetyl ether, diethylesyl peg 3.

For example as vegetable oils it can contain elements or combinations of elements selected from among olive oil, soybean oil, mango oil, sunflower seed oil, cocoa butter.

In addition the cosmetic product can comprise further elements or combinations of elements that have the functions of coloring, moisturizing, protecting, soothing, antiseptic, protecting against the sun, pharmacological, preserving, antioxidant, perfuming.

For example as coloring it can contain elements or combinations of elements selected from among the pigments titanium dioxide, iron oxides, ultramarine blue, manganese violet, chromium oxide, chromic hydroxide; among the lakes FD&C red 7, FD&C blue 1, FD&C yellow 5; among the mica-titanium dioxide pearls, mica-titanium dioxide-iron oxides, mica-iron oxides, fluorphogopite synthetic-titanium dioxide. Should the above pigments be added to the composition the product will be opaque.

If for example as coloring, elements or combinations of elements selected from among the lakes FD&C red 7, FD&C blue 1, FD&C yellow 5 in suitable percentages (for example <0.1%) are added to the composition the product will keep its transparency at the same time having a light shade of color.

For example as moisturizing agents it can contain elements or combinations of elements selected from among glycerin, hyaluronic acid.

For example as protective agents it can contain elements or combinations of elements selected from among ceramides and vitamin F.

For example as smoothing agents it can contain elements or combinations of elements selected from among alpha bisabolol, chamomile extract, escine.

For example as antiseptic agents it can contain elements or combinations of elements selected from among zeolites, farnesol.

For example as sun-protection agents it can contain elements or combinations of elements selected from among titanium dioxide, zinc oxide, octyl metoxycinamate.

For example as preserving agents and antioxidants it can contain elements or combinations of elements selected from among methylparabene, propylparabene, ascorbil palmitate, alpha tocopherol.

Several forms of embodiment of the cosmetic product are given below in accordance with the present invention, illustrated as non-limiting examples. In the following examples those numbered 1, 2 and 3 are transparent, as they do not contain pigment, while the examples 4 and 5 are colored and opaque.

EXAMPLE NO. 1

| Formula 1 | % |
| --- | --- |
| Octyldodecanol | 64.2 |
| Octyldodecyl lactate | 20.0 |
| Ethylcellulose | 5.5 |
| Diisostearyl malate | 2.0 |
| Dibutyl lauroyl glutamide | 6.5 |
| Triisostearin | 1.5 |
| Bisabolol | 0.1 |
| Flavor | 0.2 |
| TOTAL | 100 |

EXAMPLE NO. 2

| Formula 2 | % |
| --- | --- |
| Polybutene | 49.0 |
| Octyldodecyl lactate | 14.0 |
| Octyldodecanol | 19.0 |
| Ethylcellulose | 2.0 |
| Polyglyceryl 3 diisoste | 4.0 |
| Dibutyl lauroyl glutamide | 7.5 |
| Triisostearyl citrate | 2.0 |
| Tridacyl octanoate | 2.0 |
| Bisabolol | 0.3 |
| Flavor | 0.2 |
| TOTAL | 100 |

EXAMPLE NO. 3

| Formula 3 | % |
| --- | --- |
| Isocetyl alcohol | 19.0 |
| C12-15 alkyl benzoate | 9.0 |
| Diisostearyl malate | 16.2 |
| Ethyl cellulose | 1.5 |
| Neopentyl glycol dioctanoate | 2.0 |
| Dibutyl lauroyl glutamide | 7.0 |
| Polybutene | 45.0 |
| Bisabolol | 0.1 |
| Flavor | 0.2 |
| TOTAL | 100 |

EXAMPLE NO. 4

| Formula 4 | % |
| --- | --- |
| Octyldodecanol | 63.0 |
| FD&C red 7 | 1.2 |
| Octyldodecyl lactate | 20.0 |
| Ethyl cellulose | 5.5 |
| Diisostearyl malate | 2.0 |
| Dibutyl lauroyl glutamide | 6.5 |
| Triisostearin | 1.4 |
| Parapropile | 0.1 |
| Bisabolol | 0.1 |
| Flavor | 0.2 |
| TOTAL | 100 |

EXAMPLE NO. 5

| Formula 5 | % |
| --- | --- |
| Octyldodecanol | 48.9 |
| Titaniun dioxide | 5.0 |
| Octyldodecyl lactate | 30.0 |
| Ethyl cellulose | 3.5 |
| Diisostearyl malate | 4.0 |
| Dibutyl lauroyl glutamide | 5.0 |
| Triisostearin | 3.0 |
| Bisabolol | 0.1 |
| Flavor | 0.5 |
| TOTAL | 100 |

The product is prepared by mixing the ingredients desired in appropriate phases and is stirred continually for approximately 30 minutes at a temperature of between 80° C. and 125° C.

The product becomes solid after being poured into special molds and cooled at room temperature.

The invention claimed is:

1. A solid cosmetic product, comprising the following ingredients:

from 1% to 10% of ethyl cellulose;

from 4% to 10% of dibutyl lauroyl glutamide;

from 30% to 80% of non-polar organic liquids, wherein said non-polar organic liquids comprise elements or combinations of elements selected from the group consisting of octyl dodecanol, diisostearyl malate and octyl dodecyl lactate, further comprising elements or combination of elements selected from the group consisting of pigments, wherein the pigments are titanium dioxides, iron oxides, ultramarine blue, chromium oxide, chromic hydroxide; among the lakes FD&C red 7, FD&C blue 1, FD&C or yellow 5; pearls, where in pearls are mica-titanium dioxide, mica-titanium trioxide-iron oxides, mica-iron oxides or fluorphogopite synthetic-titanium dioxide; colorings, moisturizers, protection agents, smoothing agents; antiseptics, sun-protection agents, preserving agents, antioxidants and perfume agents.

2. The solid cosmetic product in accordance with claim 1, wherein it is transparent.

* * * * *